United States Patent [19]

Jalonen

[11] Patent Number: 5,660,665
[45] Date of Patent: Aug. 26, 1997

[54] ROTATING TRANSFER ROLL WITH ROTATING EXTENSIBLE PLATEN

[75] Inventor: Alvin Charles Jalonen, Appleton, Wis.

[73] Assignee: Kimberly-Clark Corporation, Neenah, Wis.

[21] Appl. No.: 574,595

[22] Filed: Dec. 15, 1995

[51] Int. Cl.$^6$ .................... B32B 31/10; B32B 31/18
[52] U.S. Cl. .................... 156/163; 156/164; 156/229; 156/256; 156/264; 156/265; 156/285; 156/494; 156/496; 156/519
[58] Field of Search ................ 156/161, 163, 156/164, 229, 256, 264, 265, 285, 308.4, 494, 495, 496, 517, 519, 520

[56] References Cited

U.S. PATENT DOCUMENTS

| | | | |
|---|---|---|---|
| 3,560,292 | 2/1971 | Butter | 156/229 |
| 3,604,015 | 9/1971 | Dove | 2/224 |
| 3,828,367 | 8/1974 | Bourgeois | 2/224 |
| 3,833,973 | 9/1974 | Schwarz | 26/59 |
| 4,284,454 | 8/1981 | Joa | 156/163 |
| 4,285,747 | 8/1981 | Rega | 156/164 |
| 4,523,969 | 6/1985 | Spencer | 156/161 |
| 4,572,043 | 2/1986 | Bianco | 83/18 |
| 4,574,022 | 3/1986 | Johnson et al. | 156/164 |
| 4,608,115 | 8/1986 | Schroth et al. | 156/519 |
| 4,642,151 | 2/1987 | Coenen | 156/164 |
| 4,735,673 | 4/1988 | Piron | 156/496 |
| 4,925,520 | 5/1990 | Beaudoin et al. | 156/494 |
| 4,943,340 | 7/1990 | Ujimoto et al. | 156/496 |
| 5,043,036 | 8/1991 | Swenson | 156/160 |
| 5,091,039 | 2/1992 | Ujimoto et al. | 156/519 |
| 5,296,080 | 3/1994 | Merkatoris et al. | 156/496 |
| 5,407,507 | 4/1995 | Ball | 156/163 |

FOREIGN PATENT DOCUMENTS

| | | |
|---|---|---|
| 0139620 | 5/1985 | European Pat. Off. . |
| 0236032 | 9/1987 | European Pat. Off. . |
| 0338662 | 10/1989 | European Pat. Off. . |
| 0443244 | 8/1991 | European Pat. Off. . |

*Primary Examiner*—James Sells
*Attorney, Agent, or Firm*—Thomas D. Wilhelm; Brian R. Tumm

[57] ABSTRACT

Apparatus including a rotating base roll for applying at least one stretched strip of a first material to a base web comprising a second material and moving continuously in first direction. The discrete length strip is cut, on the rotating roll, from a continuous ribbon, is rotated on the base roll to a desired orientation, and is stretched to a desired length. The apparatus includes the rotating roll feed apparatus for feeding the continuous ribbon to a circumferential engagement with the rotating roll, a cutter for cutting the discrete-length strips from the continuous ribbon, at least one rotating extensible platen mounted on, and rotating with the rotating roll, and an applicator rotating in concert with the rotating base roll, for applying the cut, rotated, and stretched strips to the base web.

26 Claims, 6 Drawing Sheets

ROTATING TRANSFER ROLL WITH ROTATING EXTENSIBLE PLATEN

FIELD OF THE INVENTION

This invention relates to apparatus for carrying discrete articles on a rotating base roll toward a receiving surface of a receiving web, and transferring the articles to the receiving surface. More specifically, the invention relates to receiving discrete strips of a material cut from a continuously moving endless feed web, rotating and stretching the strips of material, and transferring the stretched strips of material in the rotated orientation, to a continuously moving receiving web with the lengths of the strips oriented transverse to the direction of movement of the receiving web.

BACKGROUND OF THE INVENTION

The desirability of applying elastic of various types to garments to assist in e.g. fitting of the garments to the wearer is well known. The traditional method of securing elastic to a garment is by sewing the elastic to the garment material. The material is either gathered and the elastic is applied in a relaxed condition or the material is maintained flat and the elastic is applied in a stretched condition. The sewing of the elastic to the garment material, whether the sewing is done by hand or by machine, is slow and therefore costly in terms of the labor required.

In relatively modern technology relating to disposable garments, elastic strip material has been bonded to sheet material by the use of adhesives or heat or sonic bonding. These approaches have been commercially successful where the elastic strips have been applied with their lengths in the direction of movement of the sheet material from which the garment is formed. Efforts have also been made to apply elastic strip material with all or a portion of its length transverse to the direction of movement of the garment sheet material. Such efforts have seen limited application. An example of this approach is illustrated in U.S. Pat. No. 4,608,115 Schroth et al., herein incorporated by reference in its entirety. In the Schroth et al. patent, an unstretched elastic ribbon is fed to a revolving roll having a first axis and placed as discrete strips on platens mounted on the revolving roll. The platens revolve with the revolving roll, and each platen rotates 90 degrees about a second axis intersecting the first axis and extending through the platen, and then deposits its discrete strip or strips on a continuous traveling web, with the strips oriented transverse to the with machine direction of the traveling web.

A limitation of the Schroth et al. teaching is that the strips of ribbon material can only be placed on the advancing continuous web in the stretch condition in which they are received at the platen. Thus, if the strips are relaxed when received on the platen, the strips are relaxed when placed on the web. The platens taught in Schroth et al. cannot stretch the strips of material prior to placing them on the advancing continuous web. However, it is preferred to apply e.g. elastic strips to a web in a stretched condition where the web is a precursor for making disposable garments therefrom. Applying elastic strips in stretched condition allows the receiving web to be laid out flat, rather than requiring the web to be gathered, when the elastic strips are applied.

The invention disclosed herein is an improvement over the teaching of Schroth et al. in that the strips of material are received on the platen in a relaxed condition, and are stretched on the platen prior to placing the strips on the advancing continuous web.

SUMMARY OF THE DISCLOSURE

It is an object of the invention to provide apparatus in which discrete strips of extensible material are carried on a rotating base roll and, while being carried, are stretched, and rotated from a first orientation to a second orientation, and transferred from the base roll to an advancing continuous web.

It is another object of the invention to provide such apparatus in which the discrete strips of extensible material are carried on platens mounted on the base roll, the base roll having a first axis of rotation, each platen having a second axis of rotation passing through the first axis, each platen being individually driven for stretching, and concurrent rotation about the second axis.

Certain objects are achieved in embodiments comprehending apparatus for applying to a web of a first material, moving in a first direction, at least one discrete strip of a second material stretched in the with machine direction of the second material, the apparatus comprising a base roll rotatable about an axis; feed apparatus feeding the second material into circumferential engagement with the base roll; at least one extensible platen disposed on the base roll and rotating with the base roll about the axis, the feed apparatus delivering the discrete strip to the at least one extensible platen, the extensible platen holding the discrete strip thereto, and extending from a retracted configuration to an extended configuration while rotating with the base roll about the axis, thus stretching the discrete strip from a first retracted condition to a second stretched condition; and transfer apparatus for transferring the discrete strip, in the stretched condition, from the base roll to the web.

In preferred embodiments, the platen is a rotating extensible platen, rotating about a second axis extending from the first axis and passing through the platen, and thereby rotating from a first orientation to a second orientation about the second axis while rotating with the base roll about the first axis, thus stretching the discrete strip and correspondingly rotating the discrete strip to the second orientation.

Preferably, the apparatus includes a first retaining means such as vacuum source and connecting vacuum passages, leading to receiving surfaces on the platen, for retaining the discrete strip on the extensible platen until the discrete strip is transferred to the web.

Further, the invention may include a second retaining means, such as vacuum source and connecting vacuum passages, for retaining a length of the second material in circumferential engagement with the base roll prior to the length of material being placed and retained on a respective platen.

Preferred apparatus comprises a platen base mounted to a vacuum plate, first and second opposing platen body members mounted for sliding engagement with respect to the platen base from the retracted configuration to the extended configuration, the first and second platen body members further comprising cooperating respective first and second receiving surfaces for cooperatively receiving the discrete strip on the combination of the first and second platen body members, and vacuum communication passages communicating vacuum from a vacuum source through the vacuum plate, and thence through the platen base, to the first and second platen body members at the first and second receiving surfaces, for holding respective first and second portions of the discrete strip to the respective first and second receiving surfaces of the respective first and second platen body members and thereby stretching the discrete strip in the with machine direction of the discrete strip as the platen body members are moved from the retracted configuration to the extended configuration, and rotated about the second axis.

Preferably, the feed apparatus comprises supply apparatus for providing a continuous length of the second material, a feed roll for feeding the second material circumferentially to the base roll, and a cutter for cutting the continuous length of the second material into discrete strips.

The drive apparatus preferably comprises means maintaining the first and second platen body members in the retracted configuration and in the first orientation until the discrete strip is received on the first and second receiving surfaces, means for extending the first and second platen body members from the retracted configuration to the extended configuration and rotating the first and second platen body members from the first orientation to the second orientation, means for maintaining the first and second platen body members in the extended configuration, and in the second orientation, until the respective discrete strip is transferred to the web, and means for returning the first and second platen body members to the retracted configuration in the first orientation.

Further to preferred apparatus, the vacuum apparatus comprises control means controlling application and removal of vacuum to and from the circumferential portion of the base roll.

The invention may comprise the rotating extensible platen being in surface-to-surface engagement with a vacuum plate, the platen comprising a platen base including a slide member, first and second opposing platen body members including respective first and second grooves, in the platen body members, receiving the slide member and thereby mounting the platen body members to the platen base for sliding engagement therewith, the vacuum plate and the platen body members comprising first and second cam surfaces and respective first and second cam followers engaged therewith, effecting extension of the first and second platen body members away from each other upon rotation of the platen about the second axis, including rotation of the first and second platen body members.

In a second family of embodiments, the invention comprehends a method of applying to a web of a first material, moving in a first direction, a discrete strip of a second material oriented transverse to the web, the discrete strip being stretched in the with machine direction of the second material, the method comprising the steps of rotating a base roll about a first axis; feeding the second material into circumferential engagement with the base roll, and onto a rotating extensible platen disposed on the base roll and rotating with the base roll about the first axis, and thereby delivering the second material to the platen as a discrete strip; holding the discrete strip to the platen; while holding the discrete strip to the platen, rotating the platen with the base roll about the first axis, and transmitting drive force to the platen and thereby (i) rotating the platen with respect to a second axis extending from the first axis and passing through the platen (ii) and extending the platen from a retracted configuration to an extended configuration, thereby transposing the discrete strip from a first retracted condition at a first direction of orientation with respect to the second axis to a second stretched condition at a second direction of orientation with respect to the second axis; and transferring the discrete strip in the stretched and rotated condition from the base roll to the web.

Preferably, the method includes retaining the discrete strip on the rotating extensible platen until the discrete strip is transferred to the web.

Also preferably, the method includes receiving the discrete strip on first and second receiving surfaces of the platen, and holding the strip, preferably with vacuum, on the receiving surfaces while rotating the receiving surfaces, and thus the strip, about the second axis and sliding the first and second platen body members with respect to the platen base and thereby stretching the strip in the with machine direction of the strip as the platen body members are moved from the retracted configuration to the extended configuration.

Preferred methods include maintaining the first and second platen body members in the retracted configuration and in the first orientation until the discrete strip of the second material is received on the first and second receiving surfaces, extending the first and second platen body members from the retracted configuration to the extended configuration and rotating the first and second platen body members from the first orientation to the second orientation, maintaining the first and second platen body members in the extended configuration in the second orientation until the discrete strip is transferred to the web, and returning the first and second platen body members to the retracted configuration in the first orientation.

Figure 1:
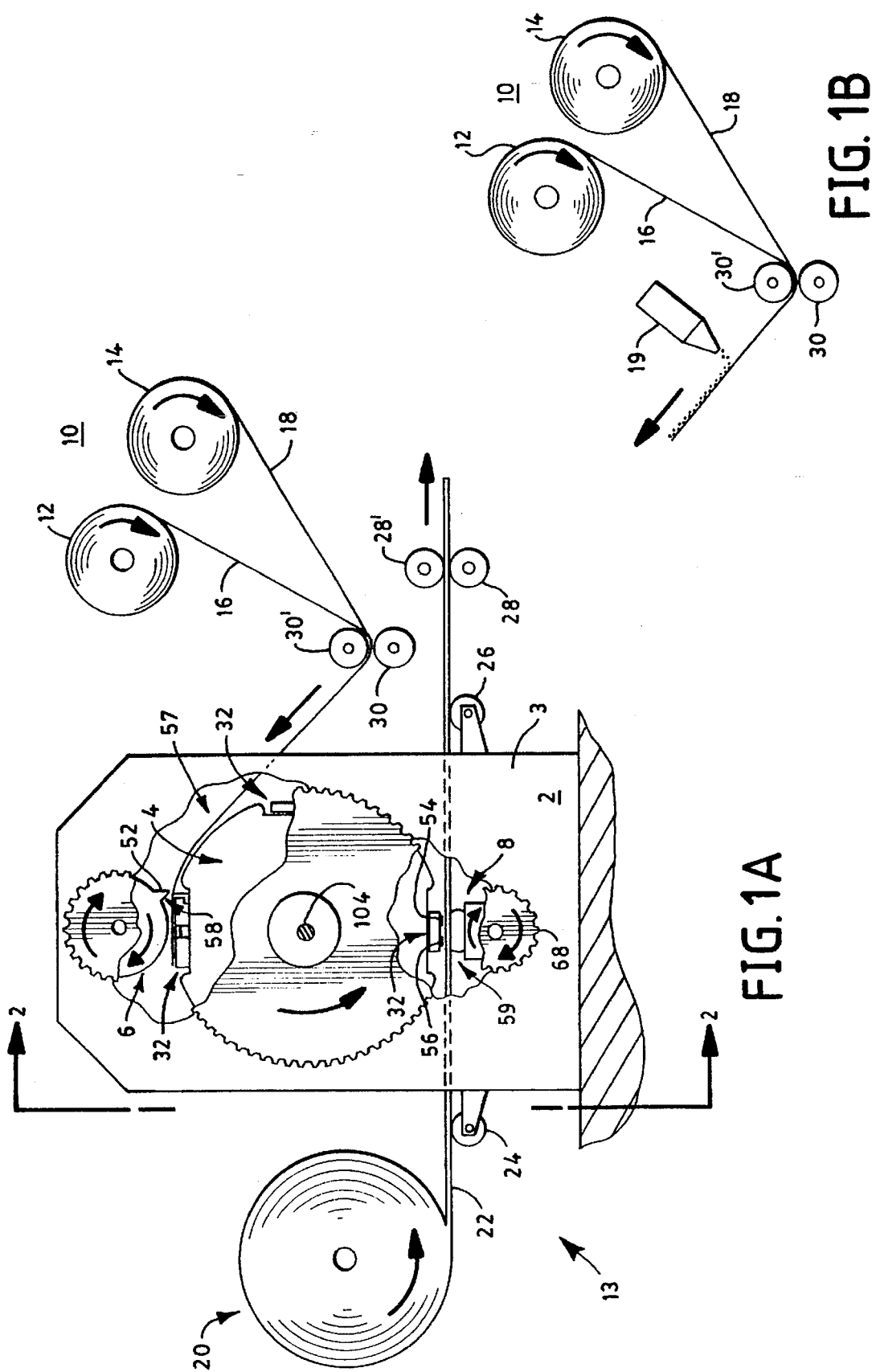
FIG. 1A shows a side elevation of applying apparatus of the invention, including a ribbon supply, a web supply, and a base roll.
FIG. 1B shows a side elevation of an alternate embodiment of the ribbon supply.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

Figure 2:
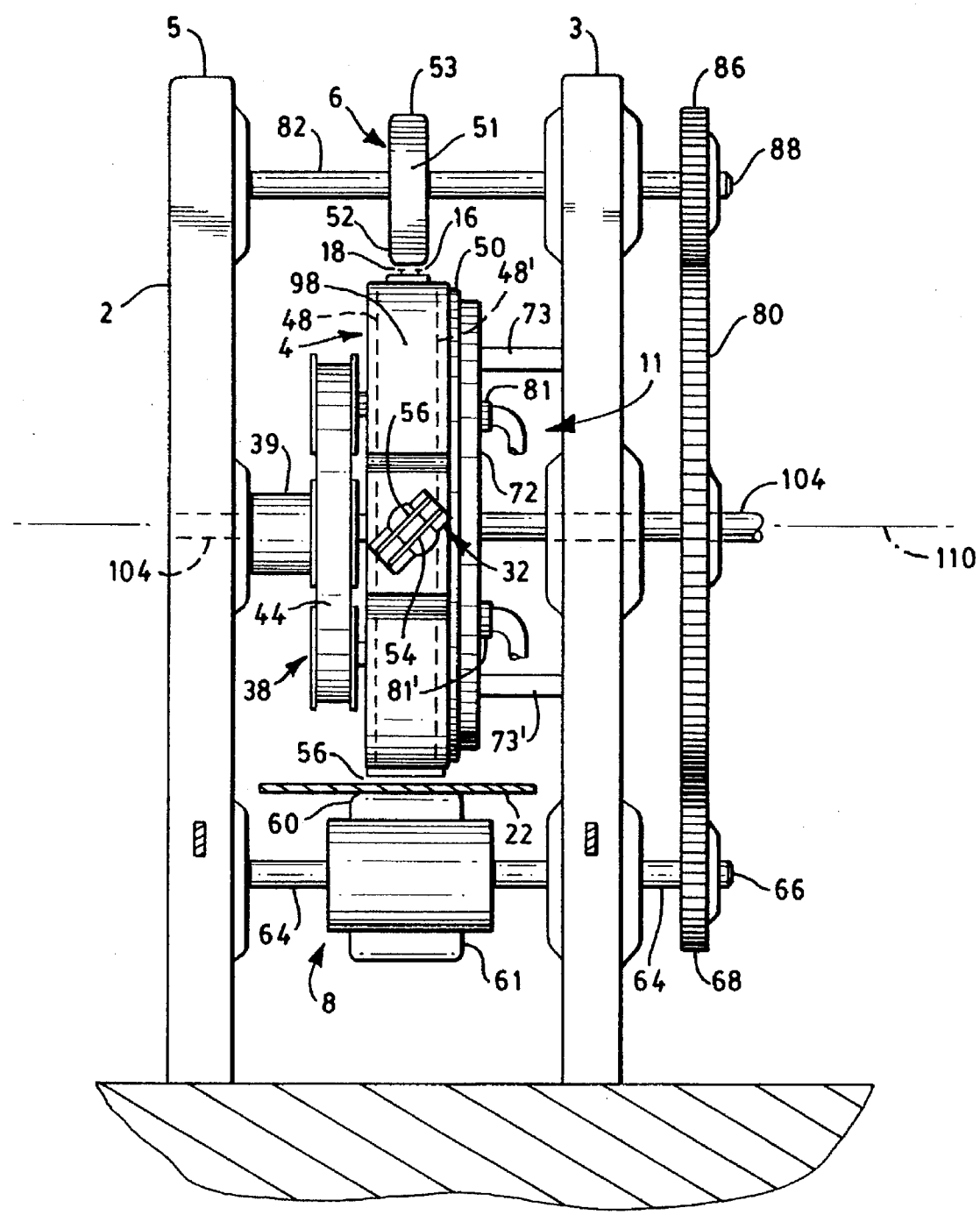
FIG. 2 is an elevation of a base roll of the invention, taken at 2—2 of FIG. 1A.

Referring generally to FIGS. 1A and 2, apparatus of the invention is shown having a frame 2, on which a base roll 4 is mounted. A cutting roll 6 and an applicator 8 are rotatably mounted on frame 2 at upper and lower areas of the frame, with the base roll 4 disposed therebetween. Endless ribbon material supply 10 including ribbon supply rolls 12 and 14 are rotatably supported on suitable supports (not shown). Supply rolls 12 and 14 continuously supply ribbons 16, 18 to the base roll 4. The rolls 12, 14 rotate in the directions shown by the arrows in FIG. 1A, feeding ribbons 16, 18 to the roll 4. A web supply 13 including a web supply roll 20 is rotatably supported by suitable means not shown. The web supply is provided for continuously feeding an endless web 22 of material into engagement with the base roll 4 between the base roll 4 and the applicator 8.

The base roll 4 is mounted on drive shaft 104 which rotates about its centerline axis 110 between spaced side walls 3 and 5 of the frame 2. Shaft 104 is journalled in bearings (not shown) on walls 3 and 5. The shaft 104 projects through the wall 3 and is rotatably driven to rotate the base roll 4 in continuous manner by a suitable drive (not shown). Base roll 4 comprises a pair of spaced apart side plates 48, 48' affixed to the shaft 104 and a plurality of slip plates 98 (See also FIGS. 3A and 3B) spaced at equal distances about the circumference of the base roll 4. The slip plates span and are affixed to each of the side plates 48, 48'. Each of the slip plates has an outward facing surface 100. Vacuum plates 78 are positioned between adjacent pairs of slip plates, as illustrated in FIG. 3B, and are also affixed to each of the side plates 48, 48'. As the base roll 4 rotates through each full revolution, it sequentially passes through feed station 57, cutting station 58, and transferring station 59.

Figure 3A:
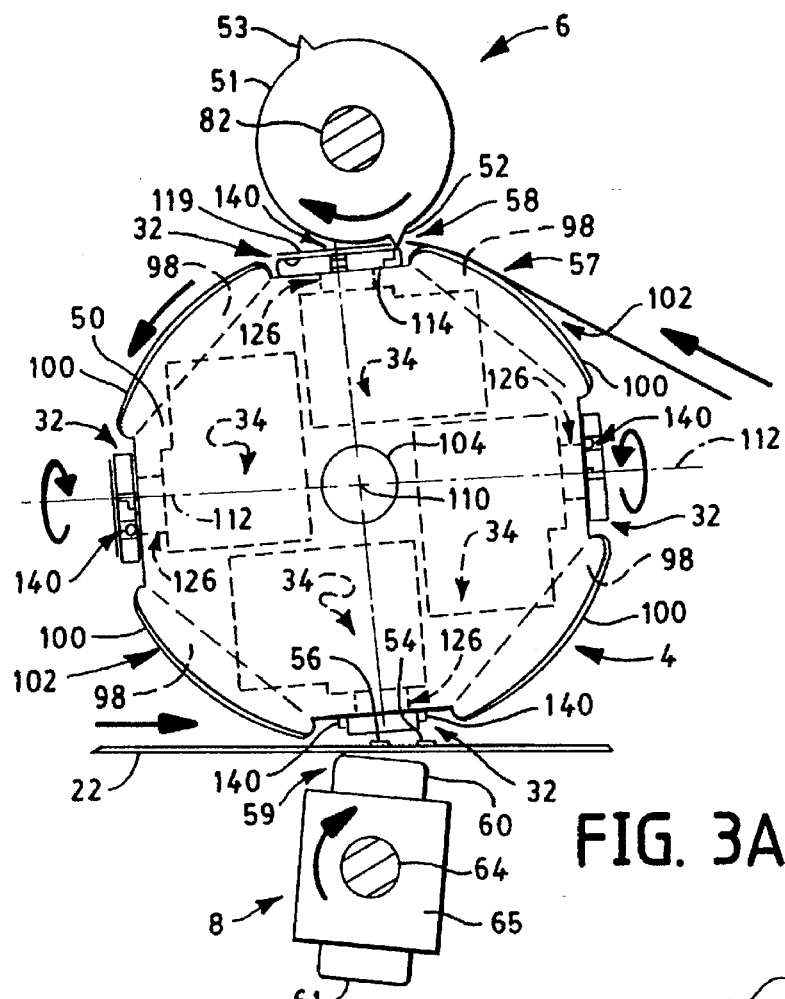
FIG. 3A is a side elevation of the base roll of the invention.
Figure 3B:
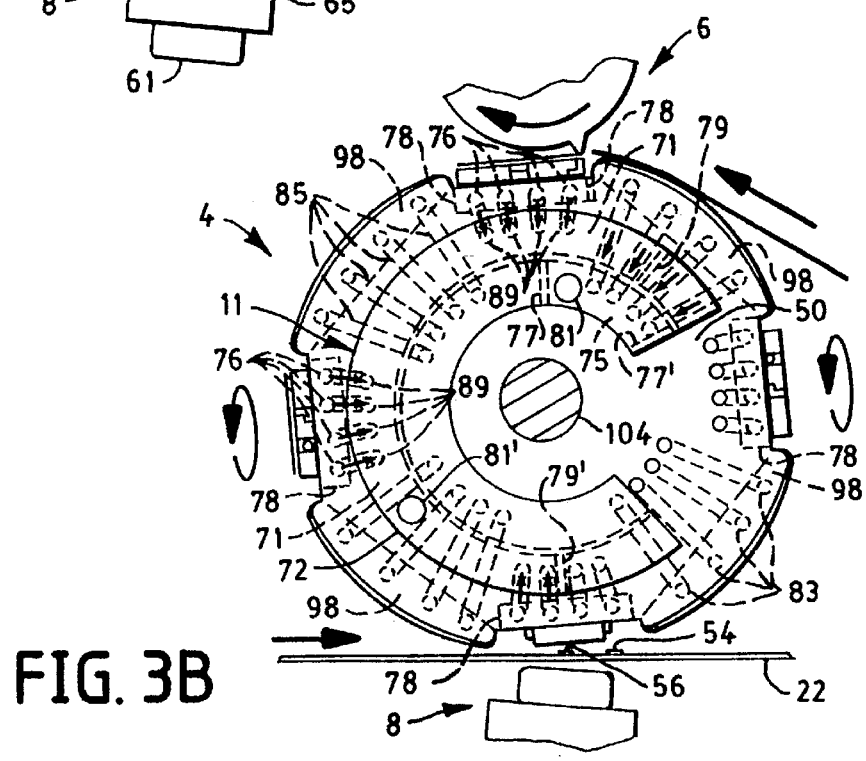
FIG. 3B is a side elevation of the base roll illustrating a vacuum system for holding the ribbon, and discrete strips of the ribbon, on the base roll.

Mounted on the base roll 4 are a plurality of rotating extensible platens 32, shown in FIGS. 3A and 3B, for receiving discrete strips 54, 56 of the endless ribbons 16, 18 as cut by cutting roll 6, carrying, rotating, and stretching the discrete strips 54, 56, and transferring the strips to the web 22 at applicator 8. Each platen 32 is directly mounted on a vacuum plate 78 between an adjacent pair of slip plates along the circumference of the base roll 4. The slip plates 98 and the platens 32 together form the outer circumferential surface 102 of the roll 4.

Platens 32 rotate about respective axes 112 that extend from axis 110 of shaft 104 and pass through the respective platens 32. Axes 112 preferably define respective perpendicular angles with axis 110. In the embodiment illustrated, the axes 112 of rotation also lie along lines radially extending from the axis 110. Because the platens 32 bear directly against the vacuum plates on which they are mounted, when the platens are rotated, they slidably move along the outer surfaces of the respective vacuum plates 78.

One of the platens 32 is shown in greater detail in FIGS. 4, 4A, 4B, 5, and 6. Each platen 32 includes a generally rectangular body 31 and a circular base 35. The circular base 35 has a pair of openings 147, 149 extending therethrough to an inner surface 117. The inner surface 117 faces in the direction of and closes one end of an opening 84 in the vacuum plate 78.

Figure 4:
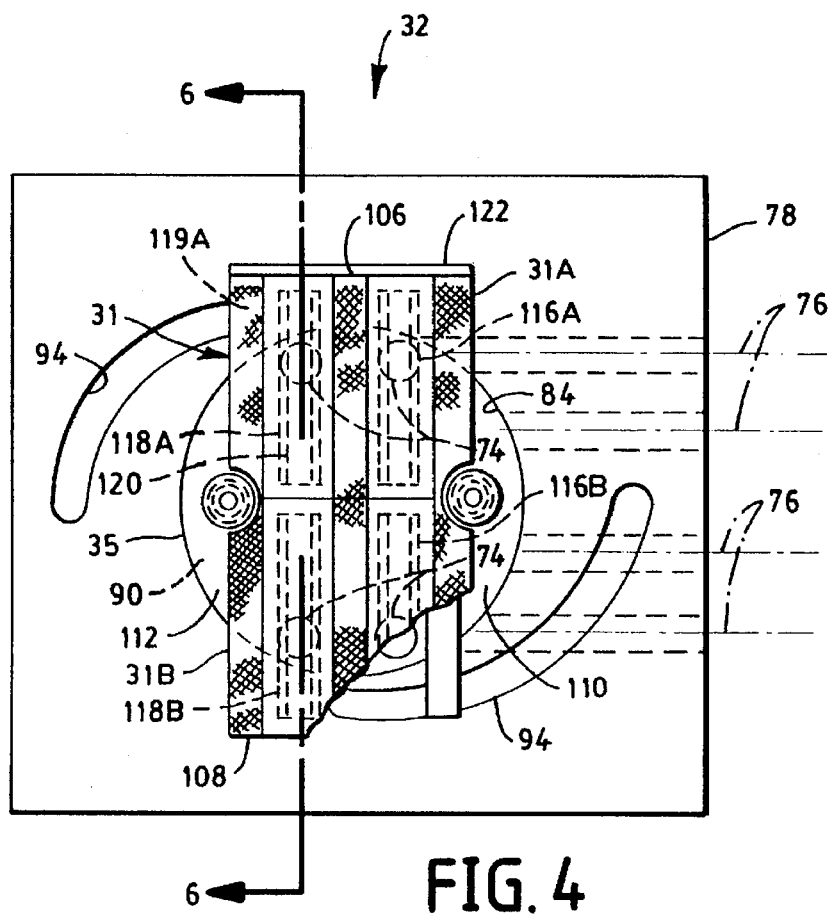
FIG. 4 is a plan view, with parts cutaway, of an extensible platen mounted on the base roll of FIG. 3A, the platen being shown in the retracted configuration, holding two strips of material.
Figure 4A:
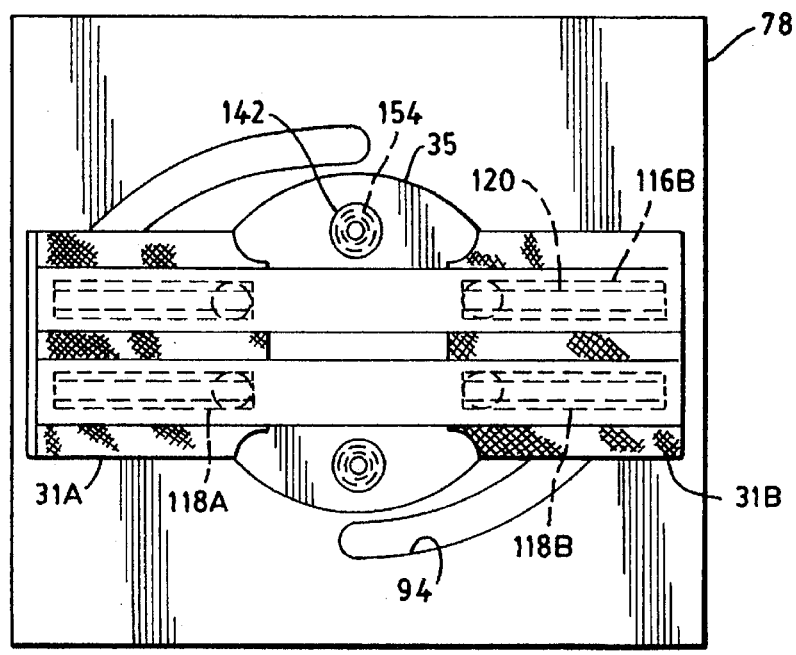
FIG. 4A is a plan view as in FIG. 4, with the platen extended and rotated, thus stretching the strip of material.
Figure 4B:
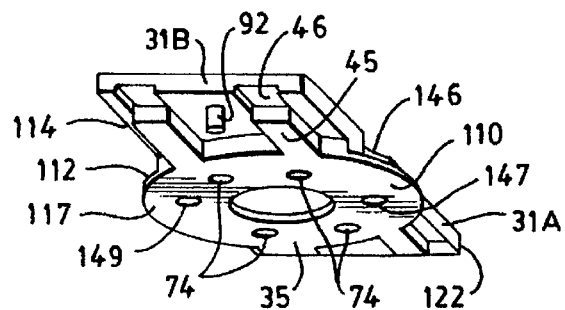
FIG. 4B is a perspective view of the extensible platen shown in FIG. 4.

The generally rectangular body 31 includes first and second body members 31A and 31B. Body members 31A, 31B are slidably mounted to the outer surface of the circular base 35 by grooves 46 in the inward facing surfaces 114 of the body members 31A, 31B received in cooperating slide members 45 mounted on the outer surface of circular base 35. FIG. 4B. Each of the body members 31A, 31B has a cam follower shaft 92 engaged with a respective cam slot 94 on respective sides of the vacuum plate 78.

Each cam slot 94 extends into the outer surface of the vacuum plate, but does not extend through the respective vacuum plate 78, whereby the vacuum in vacuum chamber 90 is preserved with respect to cam slots 94. Cam slots 94 traverse through arcs of substantially 90 degrees, with increasing radius of curvature in the direction in which the platen 32 rotates in traversing from cutting station 58 to transfer station 59, such rotation being described hereinafter.

Platen body members 31A, 31B include outer ends 106, 108 respectively, and outer surfaces 119A, 119B. Platen body member 31A includes anvil 122 at its outer end 106 and forms a portion of outer surface 119A. Formed lengthwise along the outer surfaces 119A, 119B are cooperating grooves 116A, 116B and 118A, 118B for distributing vacuum admitted through the vacuum passages 74. The platen body members also include screens 115A, 115B positioned over the outer surfaces 119A, 119B for assisting in distributing vacuum along the outer surfaces of the platen body members.

Figure 5:
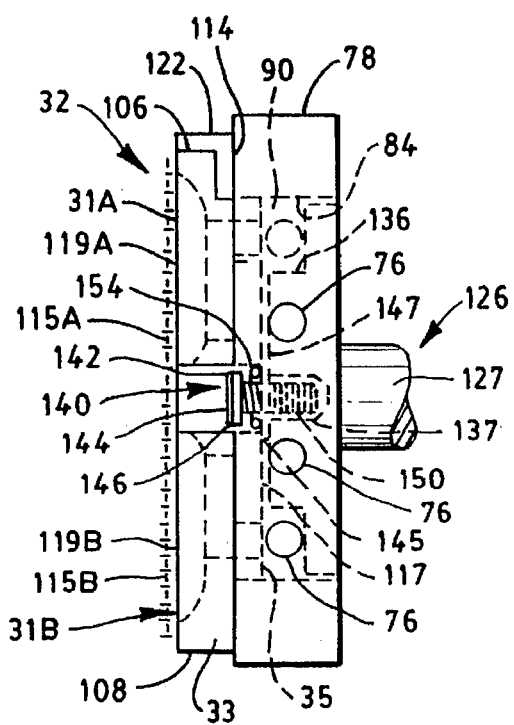
FIG. 5 is a side view of the extensible platen shown in FIG. 4.
Figure 6:
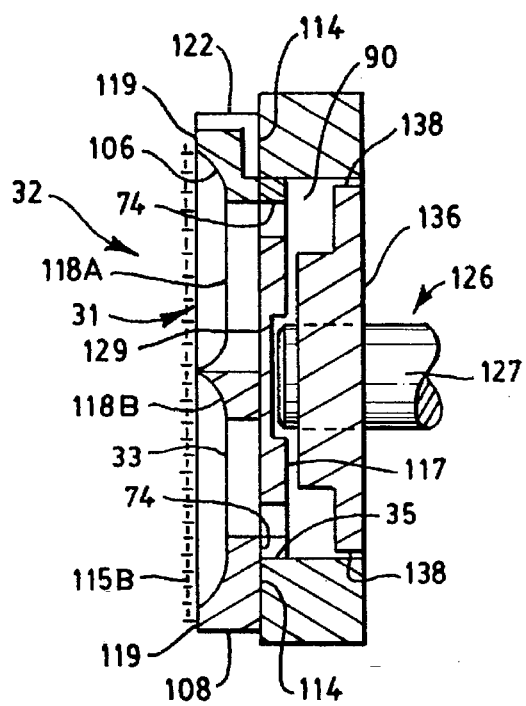
FIG. 6 is a cross section of the extensible platen shown in FIGS. 4 and 5.
Figure 8:
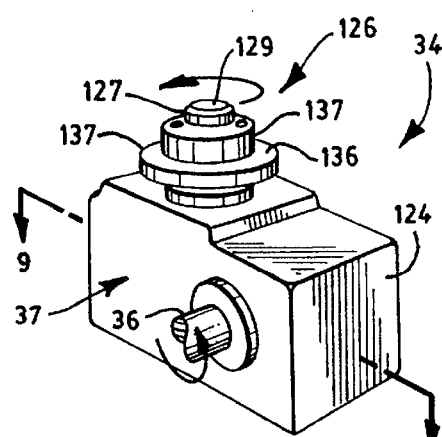
FIG. 8 is a perspective view of one of the individual drives for rotating a platen.
Figure 9:
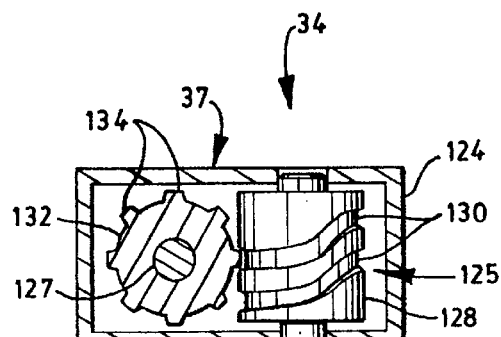
FIG. 9 is a plan view, partially in section, of one of the individual drives for rotating a platen.

With reference to FIGS. 3A, 8, and 9, a plurality of drivers 34 for providing rotating drive force to the platens 32 are illustrated, one driver 34 for each platen 32. Each driver 34 is mounted on the base roll 4 between the side plates 48, 48'. As shown in FIGS. 8 and 9, a driver 34 includes an input drive shaft 36, cam driver 37, and an output assembly 126. Each input drive shaft 36 is rotatably driven by a drive source described hereinafter. As shown in FIGS. 3A and 5, each output assembly 126 extends toward and engages a platen 32 to rotatably drive the respective platen.

The cam driver 37 is illustrated in FIGS. 8 and 9 in a simplified manner such that it shows only those components which are necessary for an understanding of its operation in conjunction with the other elements of the present invention. Also, the cam driver 37 is of a type that is well known and commercially available from various suppliers such as the Commercial Cam Division of Emerson Electric Company. Cam driver 37 comprises a housing 124, a controller 125, and a cam follower wheel 132. The controller 125 comprises a cam cylinder 128 mounted on and rotating with the input shaft 36 and having cam surfaces or grooves 130. Cam follower wheel 132 is affixed to the output shaft 127 of output assembly 126 and includes followers 134 positioned in the cam grooves 130 such that the follower wheel 132 is rotated as determined by the direction of the path of the cam grooves 130 as the cylinder 128 rotates.

It is preferred that each platen 32 have an intermittent rotating movement in which the platen does not rotate while the respective platen is at and between feed station 57 and cutting station 58 and while at the transfer station 59. The platen 32 should be rotationally stationary with respect to axis 112 at these stations to avoid rotational movement of the ribbons 16, 18 or the strips 54, 56 that might interfere with the positioning and cutting of the strips on the platen 32, or their transfer in the correct orientation to the web 22.

Further with reference to FIGS. 1A, 2, 3A, and 4, the platen 32 should be maintained at the feed and cutting stations in a first orientation in which the platen body as defined by the retracted body members 31A, 31B has its length and the vacuum grooves 116A, 116B, 118A, and 118B in alignment with the feed direction of the ribbons 16, 18 while at the feed and cutting stations, and respectively aligned with the direction of movement of the outer surface of base roll 4 as it begins its rotation about axis 110 toward transfer station 59. On the other hand, referring to FIGS. 1A, 3A, and 4A, while the platen 32 is at the transfer station 59, it should be in a second orientation in which the platen body as defined by the extended body members 31A, 31B has its length disposed at a transverse 90 degree angle to the direction of movement of the web 22, and correspondingly 90 degrees to the direction of rotation of the base roll 4. Each platen 32 rotates about the respective axis 112, through the intervening 90 degree arc, and extends the platen body members, during movement of the respective platen from the cutting station 58 to the transfer station 59. The platen 32 rotates about the respective axis 112, through the intervening reverse 90 degree arc, and thus retracts the platen body members, during movement of the respective platen from the transfer station 59 back to the feed station 57.

The intermittent rotation and positioning requirements of each platen 32 are accomplished by providing the necessary angle in the pitch of the cam groove 130, along with the appropriate arcs in cam slots 94, as followed by cam followers 92. During the time period in which the cam follower wheel 132 and therefore the platen 32 are not to move, the portion of the cam groove 130 engaging a cam follower 134 has a pitch angle of zero degrees. For the period of rotation in which the cam follower wheel 132 is to rotate such that the platen 32 rotates from the first position at the cutting station 58 to the second position at the transferring station 59, the cam groove 130 has a pitch such that the cam followers 134 advance in an axial direction within the groove 130 to provide the desired rotation to the platen 32. The particular required pitch angle of the groove 130 is determined by the speed and distances of travel of the various components of the apparatus.

The output assembly 126 of rotating driver 34 includes an adapter plate 136 (FIG. 8) affixed to output shaft 127 outside housing 124. The adapter plate 136 is positioned on the shaft 127 such that it rotates in a plane generally parallel to the outer surfaces 119. The adapter plate 136 and the end 129 of the shaft 127 are disposed toward but are spaced from the inner surface 117 on the circular base 35, including the respective inner surfaces of slide members 45. Thus, upon severing of the ribbons 16, 18, the ribbon severing force of the cutting roll 6 in the direction from the outer surface 119 to the inner surface 114 and toward the rotating driver 34, which is applied to anvil 122 and transferred to the platen 32, is not transferred by shaft 127 or adapter plate 136 of the cam driver 34. Rather, the cutting force is transferred by the inner surfaces 117 of the slide members 45 of circular base 35 to the respective vacuum plate 78. Consequently, wear on the cam driver 34 due to cutting impact is avoided and the life of the cam driver 34 is substantially longer than without such provisions for cutting force absorption.

In FIG. 3A, a plurality of force transferring means 140 are shown in engagement with platen 32. As illustrated in FIGS. 4 and 5, each force transferring means 140 comprises part of the respective output assembly 126 for transferring the rotating force of the cam driver 37 to the platen 32. The force transferring means 140 comprises a pair of shoulder bolts 142 each having a head 144, an elongated shank 145 having a threaded end 150 threaded into threaded opening 137 of the adapter plate 136, and a spring 154 concentrically mounted in compression on the shank 145 between the head 144 of the bolt 142 and the circular base 35 of the platen 32. The bolts 142 transfer rotating force of the cam driver 37 to the circular base 35 of platen 32 to rotate the platen about axis 112.

As previously discussed, the platen 32 rotates in sliding engagement on the vacuum plate 78 at inner surface 117.

The compression of the spring 154 between the head 144 of the bolt 142 and the circular base 35 provides biasing force maintaining the platen 32 in engagement with the vacuum plate 78 as the platen 32 revolves with base roll 4 about axis 110 while at the same time rotating in sliding engagement with vacuum plate 78 about axis 112.

Since the adapter plate 136 on which the force transferring apparatus 140 is mounted rotates in a plane parallel to the outer surface 119 of the body members 31A, 31B, the rotating force of the force transferring apparatus 140 is applied in a direction parallel to the plane of the outer surface 119. Conversely, rotating force in an opposite direction and in the same plane can also be applied by the platen 32 to the force transferring apparatus 140. Consequently, since the severing force of the cutting roll 6 is applied in a direction generally transverse to and preferably perpendicular to the plane of the surface 119, the severing force is not transmitted to the force transferring apparatus 140 and thereby to cam driver 37, but rather is transferred to vacuum plate 78.

Figure 7:
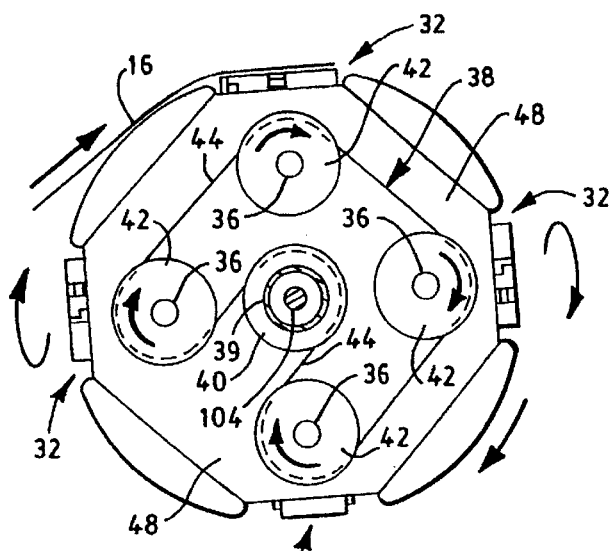
FIG. 7 is an elevation view of a belt drive for rotating the platens.

Referring now to FIGS. 2 and 7, a belt driver 38 for providing rotating drive motion to each of the rotating drivers 34 is illustrated. The belt driver 38 includes rotating drive pulleys 42 and a stationary pulley 40. The pulley 40 is supported on a cylindrical arm 39 which is mounted on side wall 5 of frame 2. The rotating drive pulleys 42 are mounted on the input shafts 36 of the rotating drivers 34. A continuous drive belt 44 is wrapped around the pulleys 42 and around the stationary pulley as shown in FIG. 7. As the shafts 36 and rotatable pulleys 42 revolve with the base roll 4, the belt 44 moves over the surface of the pulley 40 to cause the pulleys 42 to rotate. The input shafts 36 are thus rotatably driven in the direction of the arrows shown in FIG. 7, by the rotation of base roll 4.

Referring again to FIGS. 1A, 2, and 3A, the ribbon supply 10 feeds the two ribbons 16 and 18 toward the base roll 4 and onto the respective slip plate 98 over which the ribbons slip as they are initially received on the plate 98. The ribbons are fed parallel to each other and spaced apart at the distance shown for strips 54, 56 in FIG. 2. The ribbons 16, 18 are driven toward the base roll 4 by drive rolls 30, 30' at speeds such that they move onto the base roll 4 under minimal tension in a relatively relaxed condition. The ribbons 16, 18 may have a coating of pressure sensitive adhesive on their surfaces which face outward of the base roll 4. Thus, as discrete-length strips 54, 56 of the ribbons 16, 18 engage web 22, the discrete-length strips 54, 56 transfer and bond to the web 22. Alternatively, referring to FIG. 1B, ribbons 16, 18 may be supplied without adhesive. The adhesive may instead be applied to the ribbons as one of the steps in feeding the ribbons to the base roll 4. In FIG. 1B, the ribbons 16, 18 are shown being supplied by ribbon feed rolls 12, 14 to base roll 4 by drive rolls 30, 30'. Between rolls 30, 30' and the area of engagement of the ribbons 16, 18 with the base roll 4, adhesive is applied to each of the ribbons by adhesive applicator 19.

A ribbon and strip retainer system comprising a vacuum system 11, is shown in FIGS. 2 and 3B. The vacuum system 11 includes a side plate 50 affixed to and revolving with the base roll 4 and a vacuum cover 72 mounted in a stationary manner on arms 73, 73' extending from side wall 3 of the frame 2. Two vacuum supply tubes 81, 81' are connected to the vacuum cover 72 and to a suitable source of vacuum (not shown). The side plate 50 forms the inside wall of a vacuum chamber and the vacuum cover 72 forms the outside wall of the chamber. The cover 72 and the plate 50 are positioned with a very small clearance between them to avoid friction as the plate 50 rotates, but at the same time minimize loss of vacuum from within the vacuum chamber. The interior of the vacuum cover 72 is divided into two semi-circular chambers 71, 75. The end plugs 77, 77' form a relatively short chamber 75 which is connected to the vacuum pressure source through the vacuum passage 81. The vacuum chamber 71 is closed at its ends by plugs 79, 79' and is supplied from the vacuum source through passage 81'. Four vacuum passages 89 for each platen 32 extend through the plate 50 from the vacuum chamber 71 and connect to vacuum passages 76 in the vacuum plates 78. In FIGS. 4 and 5, the vacuum passages 76 are shown in vacuum plate 78 as connecting with a vacuum chamber 90 formed by the opening 84 in the vacuum plate 78, the inner surface 117 of the base 35, and the adapter plate 136. The vacuum openings 74 through the circular base 35 communicate with respective grooves 116A, 116B, 118A, and 118B through slots 120, grooves 116A, 116B, 118A, and 118B being preferably centered about slots 120. Platen body members 31A, 31B are also connected to the vacuum chamber 90. The vacuum pressure from the passages 76 is applied through the passages 74 and along the grooves 116, 118 to hold the discrete strips of ribbon 54, 56 in place on the platen 32.

As the platen 32 and side plate 50 rotate with the base roll 4, the vacuum passages 89 are connected to the vacuum chamber 71 to thereby provide vacuum to the platen 32 between the cutting station 58 and the transferring station 59. When each of the platens rotates outside the arcuate path defining the vacuum chamber 71 between plugs 79, 79', the passages 89 supplying vacuum to that platen are exposed to atmospheric pressure and the vacuum to the platen terminates.

The slip plates 98 each contain vacuum passages 83 connected to their outer surfaces 100. The vacuum passages 85 in side plate 50 connect the vacuum chamber 75 to the vacuum passages 83 in the slip plates. As the slip plates 98 revolve with side plate 50 on the base roll 4, the passages 85 move through the vacuum chamber 75 and connect vacuum to the passages 83 in the slip plates 98. Since the vacuum chamber 75 comprises a relatively short portion of the total circumference of the cover 72 in the area of feed station 57 and cutting station 58, vacuum is applied to the slip plates 98 only during the correspondingly short portion of the total circular movement of the passages 85. During the balance of the circular movement of the passages 85, the passages are open to the atmosphere. Thus, while the ribbons 16, 18 are on the slip plates 98 and moving toward feed station 58, they are held relatively immobile on the slip plates by vacuum from passages 83.

With reference to FIGS. 1A, 2, and 3A, the cutting roll 6 is shown positioned between side walls 3 and 5 of the frame 2 immediately above the base roll 4. The cutting roll 6 is supported on a rotating shaft 82 journalled in bearings (not shown) on walls 3 and 5. The shaft 82 has an end 88 extending through the wall 3 on which a gear wheel 86 is mounted in engagement with a gear wheel 80, which in turn is mounted on shaft 104. A rotating drive source (not shown) is connected to shaft 104. Rotating driving force is thus provided to the cutting roll 6 by shaft 104 through gears 80, 86, and shaft 82.

The cutting roll 6 includes a cutting wheel 51 having cutting blades 52, 53 mounted thereon. Cutting wheel 51 is rotated in the direction of the arrow shown in FIG. 1A, bringing blades 52, 53 into engagement, at the cutting station 58, with the ribbons 16, 18 and the outer surface 119 of the anvil 122 mounted on the plate 32. Discrete ribbon strips 54, 56 are thus severed from the endless ribbon material 16, 18 at the platen 32. As illustrated, each blade 52 or 53 preferably simultaneously severs the two strips 16, 18 during each movement through the cutting station 58, to form respective discrete-length individual strips 54, 56. Since the strips are severed on the anvil 122 which is mounted on the platen 32, any welding or other bonding of the ends of the strips 54, 56 to the anvil 122 as a result of the severing impact does not cause the strips 54, 56 to be pulled out of position laterally as the platen 32 rotates about the respective axis 112. After the severing of the strips 54, 56, the platen 32 carries the strips from the cutting station 58 to the transferring station 59.

The web supply 13, illustrated in FIG. 1A, includes a web supply roll 20, the support rolls 24, 26 mounted on the frame 2, and pull rolls 28, 28'. The rolls 28, 28' pull the web 22 to feed it through the transferring station 59 between the base roll 4 and the applicator 8 at a linear speed equal to that of the peripheral speed of the base roll 4 as applies at the screens 115 on the outer surfaces of platens 32. The supply roll 20 and the web 22 move in the direction of the arrows shown in FIG. 1A. The web 22 is supported as it approaches the transfer station 59 by the support roll 24 and is supported as it leaves the transfer station 59 and exits the frame 2 by support roll 26.

The applicator 8, illustrated in FIGS. 1A, 2, and 3A, is positioned between the walls 3 and 5 of frame 2 and is mounted on rotating shaft 64. The shaft 64 is journalled in bearings (not shown) on walls 3 and 5 and has an end 66 extending through the wall 3. A gear wheel 68 is affixed to shaft 64 and is positioned in engagement with the gear wheel 80 mounted on drive shaft 104. The drive source connected to the shaft 104 thus provides rotating movement to the applicator 8 through the gear wheels 80, 68 and the shaft 64. The rotation of the applicator 8 is in the direction of the arrow shown in FIG. 1A. The applicator 8 includes a body 65 through which the shaft 64 passes and striking members 60, 61 comprising a resilient material such as rubber. The striking members 60, 61 are rotated by the applicator 8 alternatively into engagement with the endless web 22 to press the web against the platens 32. Since the strips 54, 56 have an adhesive coating on their sides facing outward of the base roll 4 and thus toward the web 22 at the station 59, the compression of the web 22 against the platen causes the strips 54, 56 to transfer from the platens and adhere to the sheet due to the adhesive on the strips. The applicator 8 is shown in FIG. 2 with its striking member 60 centered below a platen at the transferring station 59. In FIG. 3A, the applicator 8 is shown as its striking member 60 moves away from the transferring station 59 after the discrete strips 54, 56 have been transferred to the sheet.

To summarize the operation of the apparatus disclosed herein, endless lengths of flexible material such as ribbons 16, 18 are continuously fed from the rolls 12, 14 through the drive rolls 30, 30' in a relatively relaxed, unextended condition into engagement with the base roll 4. As a segment of the ribbons 16, 18 engage the base roll 4, they slide over a slip plate 98 and onto a platen 32. The ribbons are held to the slip plate 98 from moving laterally out of a path in the direction of their feeding movement to the base roll by vacuum applied through vacuum passages 83 in the respective slip plate 98. As the ribbons move onto the platen 32 at the feed station 57, vacuum from the grooves 116, 118 in the platen 32 assists in maintaining the ribbons aligned with their feed path. At the feed station 57 and cutting stations 58, the platen 32 is in its first orientation to which the platen body members 31A, 31B are retracted toward each other, and the length of the platen, the slots 120, and the grooves 116A, 116B, 118A, and 118B are aligned with the feed direction of the ribbons 16, 18. The vacuum continues to be applied through the grooves 116A, 116B, 118A, and 118B to hold the severed strips 54, 56 to the platen 32 while the platen rotates on base wheel 4 about axis 110 from the cutting station 58 to the transfer station 59.

As each platen moves with the base roll 4 to the cutting station 58, the cutting roll 6 rotates one of the blades 52 or 53 into engagement with and through the ribbons 16, 18, and into engagement with the anvil 122 to thereby sever discrete strips of ribbon 54, 56 from the continuous ribbons 16, 18.

As the base roll 4 rotates, carrying the platen 32 away from the cutting station 58, the cam driver 37 begins to rotate the output assembly 126 to thereby apply rotating force to the platen 32 through the bolts 142. A partially rotated position of the platen is illustrated by platen 32 in FIGS. 2 and 3A intermediate the cutting station 58 and the transfer station 59. As the base roll 4 continues to rotate toward the transfer station 59, the platen 32 also continues to rotate about axis 112. As the platen 32 rotates about axis 112, cam followers 92 in the platen body members 31A, 31B follow cam slots 94 in vacuum plate 78, thus urging the platen body members 31A, 31B away from each other to the extended position shown in FIG. 4A. As the platen body members 31A, 31B are extended away from each other while the vacuum holds the strips 54, 56 to the outer surface of the body members 31A, 31B, the strips 54, 56 are stretched, activating restorative elastic forces in the strips 54, 56.

As the platen 32 arrives at the transfer station 59, the cam driver 37 has rotated the platen 32 to its second orientation in which the platen body members have a position at a 90 degree transverse angle to the direction of movement of the web 22. Thus, the strips 54, 56 have been rotated by the rotation of the platen 32 about axis 112, and have been stretched by the combined action of cam 92 and cam follower 94 in extending the platen body members 31A, 31B away from each other, prior to the transfer of the strips to the endless web 22. In the rotated and stretched condition, the strips are then transferred to the web 22 at the transfer station.

Due to the compression of the strips 54, 56 against the web 22 caused by the engagement of the web 22 by one of the striking members 60, 61 of the applicator 8, the strips adhere and transfer to the web. Transfer of the strips 54, 56 to the web 22 is facilitated by removal of the vacuum earlier applied to the strips 54, 56 through the grooves 116A, 116B, 118A, and 118B. Such vacuum is terminated at transfer station 59 as the respective vacuum passages reach the end of the vacuum chamber at plug 79'.

Figure 10:
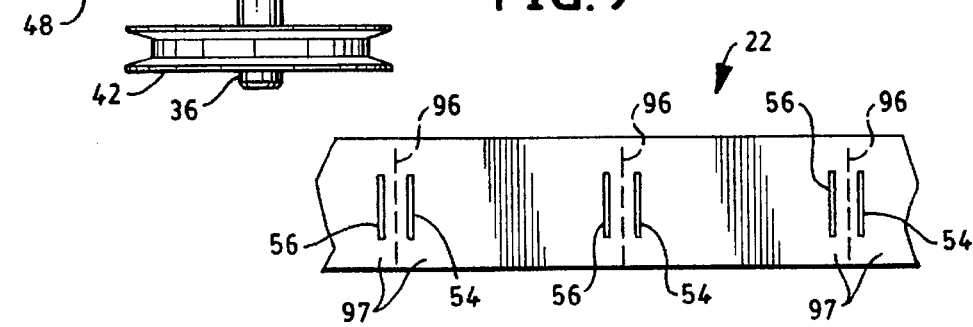
FIG. 10 is a plan view of an endless web of material on which the discrete strips may be placed in fabricating a disposable garment.

After the strips 54, 56 have been transferred to the endless web 22, the respective platen 32 moves from the transfer station 59 toward feed station 57. During such movement, cam driver 37 applies rotational force to the platen 32 through the force transferring apparatus 140 in a direction reverse to that of the force applied as the platen moved from the cutting station 58 to the transfer station 59. The platen 32 is thus rotated, prior to its reaching the feed station 57, back to its first orientation in which the vacuum grooves 116A, 116B, 118A, and 118B, and slots 120 are aligned with the path of the feeding of the continuous ribbons 16, 18. In this reverse rotation, platen body members 31A, 31B are retracted toward each other to the retracted position shown in FIG. 4 as the cam followers 92 continue to follow the cam slots 94 during rotation of the platen with respect to the corresponding vacuum plate 78.

Where the composite of the endless web 22 and the strips 54, 56 are to be utilized in fabricating a disposable garment, after the endless web 22 leaves the transfer station 59, it may be severed across its full width along the dotted lines 96 shown in FIG. 10. This severing operation produces separate blanks 97 for use in a disposable garment such as a disposable diaper. The ends of the blanks 97, where the strips 54, 56 are located, may ultimately become the front and rear waist areas of the disposable garment. In such a configuration, a single strip of material may be stretched and applied according to the present invention and then subsequently severed along dotted lines 96 shown in FIG. 10 to provide strips 54, 56. The web 22 in this use of the apparatus may preferably include a material layer such as polyethylene film.

A 90 degree transverse angle of rotation about axis 112 is preferred where the web 22 is to be used in fabricating disposable garments and the strips 54, 56 are to provide elastic properties in the waist areas of the garments. However, if it is desired to carry and transfer other types of materials utilizing the apparatus of the invention, the transverse position of such materials relative to their position when initially received on the platen or relative to the direction of movement of the receiving surface onto which they are transferred (e.g. web 22) may be at an angle other that 90 degrees. Thus, the meaning of the term "transverse" as used in this context means any orientation of the rotated strip which is at an angle relative to the position of the strip prior to its rotation about axis 112. The angle of rotation is, of course, controlled by the structure of grooves 130 in cam cylinder 128.

While the invention has been described in terms of rotating strips 54, 56, no special significance is attributed to the dimensional layout of the elements being transferred. Accordingly, the term "strip" is illustrative only, such that extensible articles of a wide variety of lengths and widths, and regular and irregular shapes can be rotated, stretched, and transferred using apparatus as defined here, subject only to routine modification to accommodate the respective layout of the articles being transferred.

Apparatus and methods have been disclosed in which a work piece can be moved at a first work station onto a rotating extensible platen mounted on a base roll rotating about a first axis 110. The article is held on the platen by vacuum while the platen rotates about a second axis 112 in combination with the outer surface of the base roll to which platen is mounted being rotated about the first axis. As the platen rotates about the axis 112 with the workpiece held to the outer surface of the platen, the platen body members on which the workpiece is held move away from each other to an extended configuration of the platen body members, thus stretching the workpiece in the with machine direction of the work piece as defined by the ribbons 16, 18 when received onto the platen. The work piece is thus stretched, and rotated by the time it reaches a second work station, namely a transfer station, where the work piece is transferred onto a web or other receiving surface.

Where it is desired to transfer an endless length of the material to the platen and sever discrete pieces of the material to be carried and transferred by the platen, an anvil is provided on the platen as part of the cutting means to sever discrete pieces of the material on the platen. The discrete pieces are held, rotated, and stretched by the platen as it moves on the outer surface of the base roll to the transfer station.

The apparatus of the invention can be utilized to rotate and stretch one or multiple strips of material simultaneously and apply them to a receiving surface/web. Consequently, two such strips are included in the illustrated embodiment, adjacent each other in a position transverse to the direction of movement of a web. A single strip or more than two strips, indeed several strips, may be used with apparatus of the invention as well. In fabricating a garment such as a disposable diaper from the sheet, the ability to position two strips of elastic material on the sheet parallel and close to each other permits simultaneous placement of elastics at the front and rear waist areas of contiguous diaper blanks.

The rotating driver for the platen, e.g. the cam driver, is entirely mounted on and rotates with the rotating base roll. Thus there is no need to have part of the driver extend from the roll and engage any stationary mechanism such as a stationary cam or cam surface. The mounting of the cam driver entirely on the rotating base roll eliminates exposure of the material being handled by the roll apparatus in such drives.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. A method of applying to a web of a first material, moving in a first direction, a discrete strip of a second material stretched in the with machine direction of the second material, the method comprising the steps of:
   (a) rotating a base roll about a first axis;
   (b) feeding the second material into circumferential engagement with the base roll, and onto a rotating extensible platen disposed on the base roll and rotating with the base roll about the first axis, and thereby delivering the second material to the platen as a discrete strip;
   (c) holding the discrete strip of the second material to the platen;
   (d) while holding the discrete strip of the second material to the platen, rotating the platen with the base roll about the first axis, and transmitting drive force to the platen and thereby
      (i) rotating the platen with respect to a second axis extending from the first axis and passing through the platen (ii) and extending the platen from a retracted configuration to an extended configuration, thereby transposing the discrete strip of the second material from a first retracted condition at a first direction of orientation with respect to the second axis to a second stretched condition at a second direction of orientation with respect to the second axis; and
   (e) transferring the discrete strip of the second material in the stretched and rotated condition from the base roll to the web.

2. A method as in claim 1, including retaining the discrete strip of the second material on the rotating extensible platen until the discrete strip of the second material is transferred to the web.

3. A method as in claim 1, the rotating extensible platen comprising a platen base mounted to a vacuum plate, first and second opposing platen body members mounted for sliding engagement with respect to the platen base from the retracted configuration to the extended configuration, the first and second platen body members further comprising cooperating respective first and second receiving surfaces for receiving the discrete strip of the second material on the combination of the first and second platen body members, and vacuum communication passages communicating vacuum from a vacuum source through the vacuum plate, and thence through the platen base, to the first and second receiving surfaces, the method including receiving the discrete strip of the second material on the first and second receiving surfaces, and holding the strip on the receiving surfaces while rotating the receiving surfaces, and thus the discrete strip, about the second axis and sliding the first and second platen body members with respect to the platen base and thereby stretching the discrete strip in the with machine direction of the discrete strip as the platen body members are moved from the retracted configuration to the extended configuration.

4. A method as in claim 1, the rotating extensible platen comprising a platen base, first and second opposing platen body members mounted for sliding engagement with respect to the platen base from the retracted configuration to the extended configuration, the first and second platen body members further comprising cooperating respective first and second receiving surfaces for receiving the discrete strip of the second material on the combination of the first and second platen body members, the method including holding respective first and second portions of the discrete strip of the second material to the respective first and second platen receiving surfaces with vacuum and thereby stretching the discrete strip of the second material in the with machine direction of the discrete strip as the platen body members are moved from the retracted configuration to the extended configuration.

5. A method as in claim 1, the rotating extensible platen comprising first and second opposing platen body members mounted for sliding engagement from the retracted configuration to the extended configuration, the first and second platen body members comprising cooperating respective first and second receiving surfaces for receiving the discrete strip on the combination of the first and second platen body members, the method including maintaining the first and second platen body members in the retracted configuration and in the first orientation until the discrete strip of the second material is received on the first and second receiving surfaces, extending the first and second platen body members from the retracted configuration to the extended configuration and rotating the first and second platen body members from the first orientation to the second orientation, maintaining the first and second platen body members in the extended configuration in the second orientation until the discrete strip of the second material is transferred to the web, and returning the first and second platen body members to the retracted configuration in the first orientation.

6. Apparatus for applying to a web of a first material, moving in a first direction, at least one discrete strip of a second material stretched in the with machine direction of the second material, said apparatus comprising:
   (a) a base roll rotatable about an axis;
   (b) feed apparatus feeding the second material into circumferential engagement with said base roll;
   (c) at least one extensible platen disposed on said base roll, rotating with said base roll about the axis, said feed apparatus delivering the at least one discrete strip of the second material to said at least one extensible platen, said at least one extensible platen holding the at least one discrete strip of the second material thereto, and extending from a retracted configuration to an extended configuration while rotating with said base roll about the axis, thus stretching the at least one discrete strip of the second material from a first retracted condition to a second stretched condition; and (d) transfer apparatus for transferring the at least one discrete strip of the second material, in the stretched condition, from said base roll to the web.

7. Apparatus as in claim 6, including first retaining means for retaining the at least one discrete strip of the second material on said extensible platen until the at least one discrete strip of the second material is transferred to the web.

8. Apparatus as in claim 7, including second retaining means for retaining a length of the second material in circumferential engagement with said base roll prior to the length of material being placed and retained on a respective said extensible platen.

9. Apparatus as in claim 7 wherein said first retaining means comprises vacuum apparatus for providing vacuum to a circumferential portion of said base roll, and thence to said extensible platen in the respective circumferential portion.

10. Apparatus as in claim 9, said extensible platen comprising a platen base mounted to a vacuum plate, first and second opposing platen body members mounted for sliding engagement with respect to said platen base from the retracted configuration to the extended configuration, said first and second platen body members further comprising cooperating respective first and second receiving surfaces for receiving the at least one discrete strip of the second material on the combination of said first and second platen body members, and vacuum communication passages communicating vacuum from a vacuum source through said vacuum plate, and thence through said platen base, to said first and second platen body members at said first and second receiving surfaces.

11. Apparatus as in claim 7, said extensible platen comprising a platen base, and first and second opposing platen body members mounted for sliding engagement with respect to said platen base, from the retracted configuration to the extended configuration while holding respective first and second portions of the at least one discrete strip of the second material to the respective first and second platen body members and thereby stretching the at least one discrete strip of the second material in the with machine direction of the discrete strip as the platen body members are moved from the retracted configuration to the extended configuration.

12. Apparatus as in claim 9, said extensible platen comprising a platen base, first and second opposing platen body members mounted for sliding engagement with respect to said platen base from the retracted configuration to the extended configuration, said first and second platen body members further comprising cooperating respective first and second receiving surfaces for receiving the at least one discrete strip of the second material on the combination of said first and second platen body members, vacuum communication passages communicating vacuum from a vacuum source through said platen base to said first and second platen body members at said first and second receiving surfaces, such that said first and second platen body members hold respective first and second portions of the at least one discrete strip of the second material to the respective first and second platen receiving surfaces with vacuum and thereby stretch the at least one discrete strip of the second material in the with machine direction of the discrete strip as the platen body members are moved from the retracted configuration to the extended configuration.

13. Apparatus as in claim 6, said feed apparatus comprising supply apparatus for providing a continuous length of the second material, a feed roll for feeding the second material circumferentially to said base roll, and a cutter for cutting the continuous length of the second material into discrete strips.

14. Apparatus as in claim 10, said apparatus comprising means for maintaining said first and second platen body members in the retracted configuration until the at least one discrete strip of the second material is received on said first and second receiving surfaces, means for extending said first and second platen body members from the retracted configuration to the extended configuration, means for maintaining said first and second platen body members in the extended configuration until the at least one discrete strip of the second material is transferred to the web, and means for returning the first and second platen body members to the retracted configuration.

15. Apparatus as in claim 9, said vacuum apparatus further comprising control means controlling application and removal of vacuum to and from said circumferential portion of said base roll.

16. Apparatus for applying to a web of a first material, moving in a first direction, at least one discrete strip of a second material stretched in the with machine direction of the second material, said apparatus comprising:

(a) a base roll rotatable about a first axis;

(b) feed apparatus feeding the second material into circumferential engagement with said base roll;

(c) at least one rotating extensible platen disposed on said base roll, a second axis extending from the first axis and passing through said at least one rotating extensible platen, said at least one rotating extensible platen rotating with said base roll about the first axis, said feed apparatus delivering the at least one discrete strip of the second material to the at least one rotating extensible platen, said at least one rotating extensible platen holding the at least one discrete strip of the second material thereto, and extending from a retracted configuration to an extended configuration and rotating about the second axis from a first orientation to a second orientation while rotating with said base roll about the first axis, thus stretching the at least one discrete strip of the second material from a first retracted condition to a second stretched condition and correspondingly rotating the at least one discrete strip of the second material to the second orientation; and (d) transfer apparatus for transferring the at least one discrete strip of the second material in the stretched and rotated condition from said base roll to the web.

17. Apparatus as in claim 16, including first retaining means for retaining the at least one discrete strip of the second material on said rotating extensible platen until the at least one discrete strip of the second material is transferred to the web.

18. Apparatus as in claim 17, including second retaining means for retaining a length of the second material in circumferential engagement with said base roll prior to the length of material being placed and retained on a respective rotating extensible platen.

19. Apparatus as in claim 17 wherein said first retaining means comprises vacuum apparatus for providing vacuum to a circumferential portion of said base roll, and thence to said rotating extensible platen in the respective circumferential portion.

20. Apparatus as in claim 19, said rotating extensible platen comprising a platen base mounted to a vacuum plate, first and second opposing platen body members mounted for sliding engagement with respect to said platen base from the retracted configuration to the extended configuration, said first and second platen body members further comprising cooperating respective first and second receiving surfaces for receiving the at least one discrete strip of the second material on the combination of said first and second platen body members, and vacuum communication passages communicating vacuum from a vacuum source through said vacuum plate, and thence through said platen base, to said first and second platen body members at said first and second receiving surfaces.

21. Apparatus as in claim 17, said rotating extensible platen comprising a platen base, and first and second opposing platen body members mounted for sliding engagement with respect to said platen base, from the retracted configuration to the extended configuration while holding respective first and second portions of the at least one discrete strip of the second material to the respective first and second platen body members and thereby stretching the at least one discrete strip of the second material in the with machine direction of the discrete strip as the platen body members are moved from the retracted configuration to the extended configuration.

22. Apparatus as in claim 19, said rotating extensible platen comprising a platen base, first and second opposing platen body members mounted for sliding engagement with respect to said platen base from the retracted configuration to the extended configuration, said first and second platen body members further comprising cooperating respective first and second receiving surfaces for receiving the at least one discrete strip of the second material on the combination of said first and second platen body members, vacuum communication passages communicating vacuum from a vacuum source through said platen base to said first and second platen body members at said first and second receiving surfaces, such that said first and second platen body members hold respective first and second portions of the at least one discrete strip of the second material to the respective first and second platen receiving surfaces with vacuum and thereby stretch the at least one discrete strip of the second material in the with machine direction of the discrete strip as the platen body members are moved from the retracted configuration to the extended configuration.

23. Apparatus as in claim 16, said feed apparatus comprising supply apparatus for providing a continuous length of the second material, a feed roll for feeding the second material circumferentially to said base roll, and a cutter for cutting the continuous length of the second material into discrete strips.

24. Apparatus as in claim 20, said apparatus comprising means for maintaining said first and second platen body members in the retracted configuration and in the first orientation until the at least one discrete strip of the second material is received on said first and second receiving surfaces, means for extending said first and second platen body members from the retracted configuration to the extended configuration and rotating said first and second platen body members from the first orientation to the second orientation, means for maintaining said first and second platen body members in the extended configuration in the second orientation until the at least one discrete strip of the second material is transferred to the web, and means for returning the first and second platen body members to the retracted configuration in the first orientation.

25. Apparatus as in claim 19, said vacuum apparatus further comprising control means controlling application and removal of vacuum to and from said circumferential portion of said base roll.

26. Apparatus as in claim 16, said rotating extensible platen being in surface-to-surface engagement with a vacuum plate, said rotating extensible platen comprising a platen base including a slide member, first and second opposing platen body members including respective first and second grooves, in said platen body members, receiving said slide member and thereby mounting said platen body members to said platen base for sliding engagement therewith, said vacuum plate and said platen body members comprising first and second cam surfaces and respective first and second cam followers engaged therewith, effecting extension of said first and second platen body members away from each other upon rotation of said platen about the second axis, including rotation of said first and second platen body members.

* * * * *